United States Patent
Peichel et al.

(10) Patent No.: US 11,660,458 B2
(45) Date of Patent: *May 30, 2023

(54) METHOD OF DETECTING PRESENCE OF IMPLANTED POWER TRANSFER COIL

(71) Applicant: Medtronic, Inc., Minneapolis, MN (US)

(72) Inventors: David J. Peichel, Minneapolis, MN (US); Jonathan P. Roberts, Coon Rapids, MN (US); Jacob A. Roe, North St Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 7 days.

This patent is subject to a terminal disclaimer.

(21) Appl. No.: 17/353,893

(22) Filed: Jun. 22, 2021

(65) Prior Publication Data

US 2021/0313847 A1    Oct. 7, 2021

Related U.S. Application Data

(63) Continuation of application No. 16/841,904, filed on Apr. 7, 2020, now Pat. No. 11,063,479.

(51) Int. Cl.
| | |
|---|---|
| *A61N 1/37* | (2006.01) |
| *A61N 1/378* | (2006.01) |
| *H02J 50/80* | (2016.01) |
| *H02J 50/90* | (2016.01) |
| *H02J 50/12* | (2016.01) |
| *A61N 1/372* | (2006.01) |

(52) U.S. Cl.
CPC ........ *A61N 1/3787* (2013.01); *A61N 1/37211* (2013.01); *H02J 50/12* (2016.02); *H02J 50/80* (2016.02); *H02J 50/90* (2016.02)

(58) Field of Classification Search
None
See application file for complete search history.

(56) References Cited

U.S. PATENT DOCUMENTS

| | | | |
|---|---|---|---|
| 8,764,621 | B2 | 7/2014 | Badstibner et al. |
| 8,862,241 | B2 | 10/2014 | Forsell |

(Continued)

OTHER PUBLICATIONS

Prosecution History from U.S. Appl. No. 16/841,904 from Feb. 19, 2021 through Jun. 21, 2021, 27 pp.

(Continued)

*Primary Examiner* — Ankit D Tejani
(74) *Attorney, Agent, or Firm* — Shumaker & Sieffert, P.A.

(57) ABSTRACT

A method and apparatus related to detecting the presence of a power transfer coil implanted in a patient are disclosed. According to the aspect, an external device of a medical implant system is provided, the external device having an external coil and processing circuitry. The processing circuitry is configured to monitor a resonance frequency associated with the external coil. When the resonance frequency changes as a distance between the external coil and an expected location of an internal coil, then the processing circuitry is configured to conclude that the internal coil has been detected. When the resonance frequency ramps up to a steady state value at a rate that falls below a rate threshold, then the processing circuitry is configured to conclude that the internal coil is connected to an internal load.

22 Claims, 8 Drawing Sheets

(56) References Cited

U.S. PATENT DOCUMENTS

| | | |
|---|---|---|
| 9,089,717 B2 | 7/2015 | Forsell |
| 10,238,468 B2 | 3/2019 | Forsell |
| 10,376,624 B2 | 8/2019 | Rudser et al. |
| 11,063,479 B1* | 7/2021 | Peichel .................. H02J 50/60 |
| 2012/0053657 A1 | 3/2012 | Parker et al. |
| 2012/0256620 A1 | 11/2012 | Oettinger |
| 2012/0277831 A1* | 11/2012 | Joshi .................. A61N 1/37223 |
| | | 607/62 |
| 2013/0289334 A1 | 10/2013 | Badstibner et al. |
| 2015/0290373 A1 | 10/2015 | Rudser et al. |
| 2016/0028248 A1 | 1/2016 | Asanuma et al. |
| 2016/0043566 A1 | 2/2016 | Terao |
| 2016/0329751 A1 | 10/2016 | Mach et al. |
| 2018/0102677 A1 | 4/2018 | Tsai et al. |
| 2018/0280708 A1 | 10/2018 | Escalona et al. |
| 2019/0076587 A1 | 3/2019 | Rudser et al. |
| 2020/0285287 A1* | 9/2020 | Han ..................... G06F 3/0346 |

OTHER PUBLICATIONS

International Search Report and Written Opinion dated Jun. 7, 2021, for corresponding International Application No. PCT/US2021/020179; International Filing Date: Mar. 1, 2021 consisting of 9-pages.

* cited by examiner

METHOD OF DETECTING PRESENCE OF IMPLANTED POWER TRANSFER COIL

CROSS-REFERENCE TO RELATED APPLICATION

This application is a continuation of U.S. application Ser. No. 16/841,904, filed Apr. 7, 2020.

FIELD

The present technology is generally related to detecting the presence of a power transfer coil implanted in a patient.

BACKGROUND

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 22 with a detachable battery 24. In operation, power is supplied from the external power transmitter 22 to the i-controller 14 via of mutual coupling of the coils 18 and 20, in order to charge i-controller 14 and to power the LVAD pump 12. The coils 18 and 20 transfer power by mutual induction of electromagnetic energy over the air and through the body. The power supplied by the external power transmitter 22 may come from the detachable battery 24 or from a wall outlet, for example.

When the external coil, e-coil 20, is aligned with the internal coil, i-coil 18, and is close to the body, there is a high degree of power transfer efficiency. When the two coils are distant and/or unaligned, power transfer efficiency declines and heat generated in the coils may increase. Also, if there is a nearby foreign metal object, energy losses may occur transferring energy to the foreign metal object. Further, if the i-coil 18 is unconnected, it is undesirable to attempt energy transfer to the i-coil 18.

SUMMARY

The techniques of this disclosure generally relate to detecting the presence of a power transfer coil implanted in a patient.

According to one aspect, a method is implemented by a medical implant system having an internal coil implanted within the body of a patient, the internal coil being capable of receiving power from an external coil outside the body, the external coil being in communication with external processing circuitry to execute steps of the method. The method includes periodically detecting a presence of the internal coil, the periodically detecting including monitoring change in a resonance frequency associated with the external coil.

According to this aspect, in some embodiments, when change in the resonance frequency indicates the presence of the internal coil, then determining connectivity of the internal coil, the determining including monitoring a rate at which the resonance frequency rises to a steady state value. In some embodiments, the method further includes detecting a presence of a metal object, the detecting the presence of the metal object including determining when the external coil is drawing increased power for a given drive current and monitoring for reception of power regulation packets from the internal coil. In some embodiments, the method further includes, when there is no reception of power regulation packets within a time interval, concluding that a metal object is present. In some embodiments, in some embodiments, the method further includes, when there is no reception of power regulation packets within a time interval, concluding that there is a fault in one or more internal components of the medical implant system. In some embodiments, the method includes sensing for acceleration of an external component of the medical implant system and when acceleration is detected, then adjusting a duty cycle of the periodically detecting. In some embodiments, the periodically detecting includes concluding that the implanted coil is present when the resonance frequency increases as the distance between an expected location of the internal coil and the location of the external coil decreases. In some embodiments, the determining connectivity includes concluding that the internal coil is connected to an internal load when the resonance frequency ramps up to the steady state value at a rate that falls below a rate threshold.

According to another aspect, a medical implant system is provided, the medical implant system having an internal coil implanted within the body of a patient, the internal coil being capable of receiving power from an external coil outside the body, the external coil being in communication with external processing circuitry. The external processing circuitry is configured to periodically detect the presence of the internal coil, the periodically detecting including monitoring change in a resonance frequency associated with the external coil.

According to this aspect, in some embodiments, when change in the resonance frequency indicates the presence of the internal coil, then the external processing circuitry is configured to determine connectivity of the internal coil, the determining including monitoring a rate at which the resonance frequency rises to a steady state value. In some embodiments, the external processing circuitry is further configured to detect a presence of a metal object, the detecting the presence of the metal object including determining when the external coil is drawing increased power for a given drive current and monitoring for reception of power regulation packets from the internal coil. In some embodiments, the external processing circuitry is further configured to, when there is no reception of power regulation packets within a time interval, conclude that a metal object is present. In some embodiments, the external processing circuitry is further configured to, when there is no reception of power regulation packets within a time interval, conclude that there is a fault in one or more internal components of the medical implant system. In some embodiments, the external processing circuitry is further configured to sense for acceleration of an external component of the medical implant system and when acceleration is detected, then adjusting a duty cycle of the periodically detecting. In some embodiments, the periodically detecting includes concluding that the implanted coil is present when the resonance frequency increases as the distance between an expected location of the internal coil and the location of the external coil decreases. In some embodiments, the determining connectivity includes concluding that the internal coil is connected to an internal load when the resonance frequency ramps up to the steady state value at a rate that falls below a rate threshold.

According to yet another aspect, an external device of a medical implant system is provided. The external device has an external coil and processing circuitry, the processing circuitry configured to monitor a resonance frequency associated with the external coil. When the resonance frequency changes as a distance between the external coil and an expected location of an internal coil, then the processing circuitry is configured to conclude that the internal coil has been detected. When the resonance frequency ramps up to a steady state value at a rate that falls below a rate threshold, then the processing circuitry is further configured to conclude that the internal coil is connected to an internal load.

According to this aspect, in some embodiments, the processing circuitry is further configured to monitor power drawn by the external coil and monitor for reception of power regulation packets. When the power drawn by the external coil increases for a given drive current and no power regulation packets have been received within a time interval, then the processing circuitry is configured to conclude that one of a metal object is present and a fault exists in an internal component of the medical implant system. In some embodiments, the processing circuitry is further configured to adjust a frequency of attempts to detect the internal coil. In some embodiments, the adjusting is based on an acceleration of the external device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
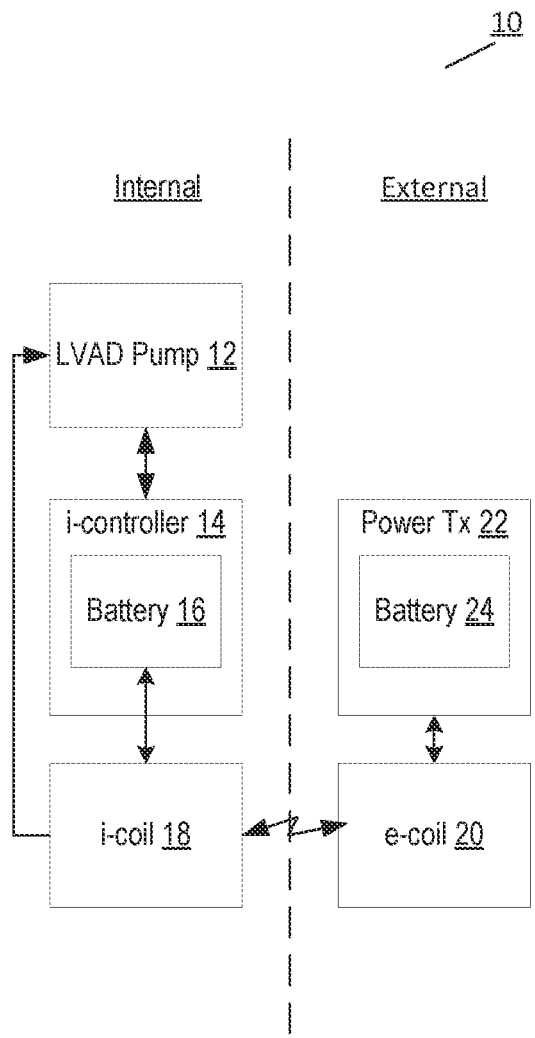
FIG. 1 is a block diagram of an LVAD implant system.
Figure 2:
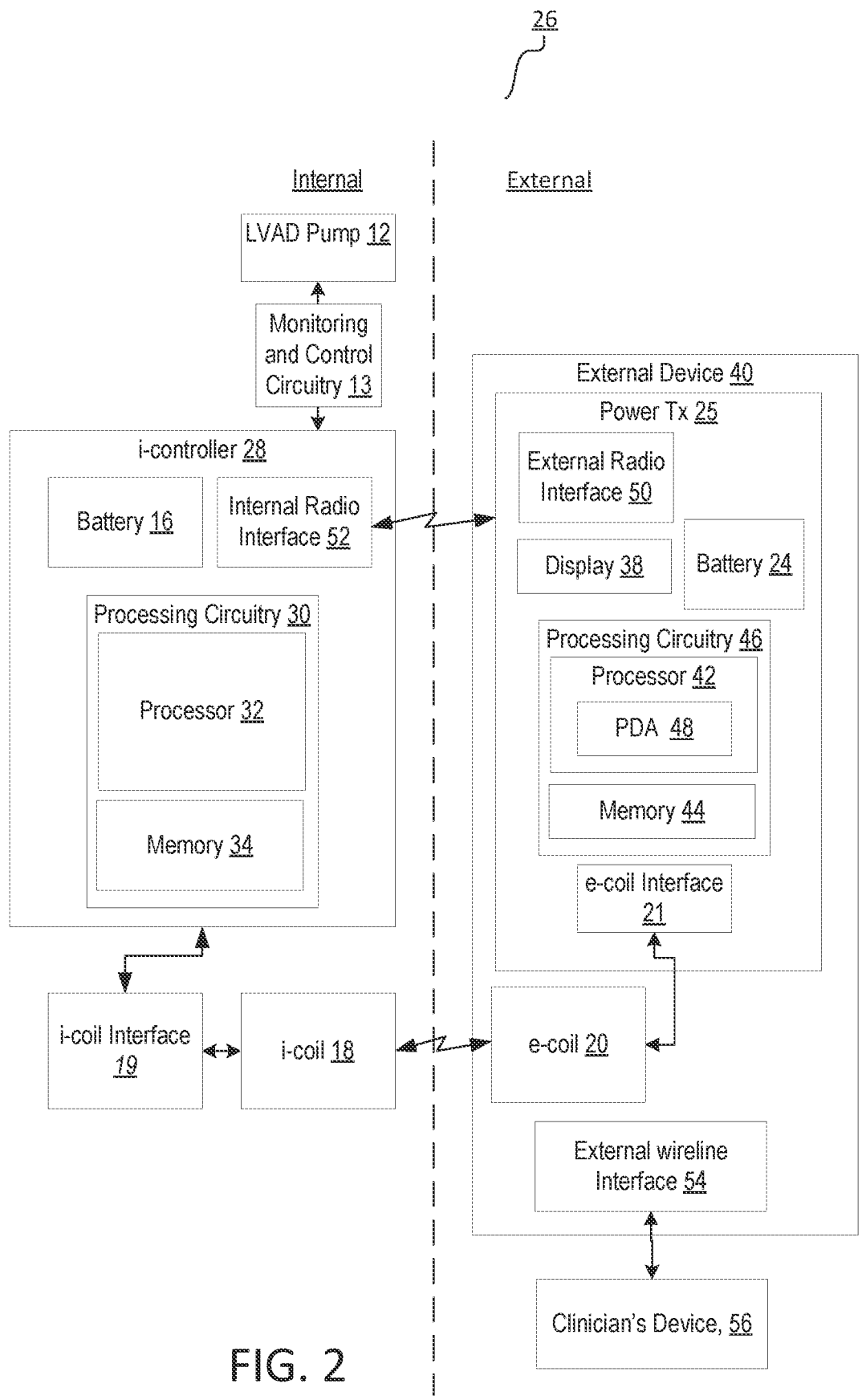
FIG. 2 is a block diagram of an LVAD implant system constructed according to principles set forth herein.

Some embodiments described herein are related to detecting the presence of a power transfer coil implanted in a patient. FIG. 2 shows a block diagram of one example configuration of an LVAD system 26 having an internal component such as an internal controller (i-controller) 28 configured to perform functions related to detecting presence of a power transfer coil. The i-controller 28 may have processing circuitry 30 which may include a processor 32 and a memory 34. The processor 32 may be configured to execute computer instructions stored in the memory 34. Those instructions may include instructions to cause the processor to perform the algorithms described in more detail below.

Information from the i-controller 28 may be sent to be displayed on an external display 38 of an external device 40, which may include a processor 42 and a memory 44 within processing circuitry 46, the external power transmitter 25 and the detachable battery 24, as well as the e-coil 20 in some embodiments. The memory 44 may be configured to store computer instructions to be executed by the processor 42 and may also be configured to store instructions for detection of presence of the i-coil 18 as well as other algorithms described below. Accordingly, the processor 42 may implement an internal coil presence detection algorithm (PDA) 48, which is configured to detect the presence of the i-coil 18.

Electrical communication of signals and power between the internal components of i-controller 28 may be via communication busses and individual electrical conductors not shown in FIG. 2. For example, a multi-conductor address bus and data bus may connect processor 32 with memory 34. In some embodiments, an i-coil interface 19 associated with i-coil 18 may be included in the set of internal components making up the LVAD system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16. Some or all functions of the i-coil interface 19 may be included in the i-controller 28 and/or the i-coil 18. Similarly, electrical communication of signals and power between the internal components of external device 40 may be by communication busses and individual electrical conductors not shown in FIG. 2. For example, a multi-conductor address bus and data bus may connect processor 42 with memory 44. In some embodiments, an e-coil interface 21 associated with e-coil 20 may be included in the set of external components making up the LVAD system 26. One purpose of e-coil interface 21 may be to modulate the alternating current applied to the e-coil 20 with signals from the processing circuitry 46 to be transmitted from the e-coil 20 to the i-coil 18 and/or to demodulate signals received by the e-coil 20 from the i-coil 18.

In some embodiments, the internal components of the LVAD system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in or on the LVAD pump 12. Information obtained from and/or about the LVAD pump 12, such as speed and temperature, may be sent to the external device 40 to be displayed by external display 38.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40 in some embodiments. Note further that some of the functions performed by processor 32 may be performed instead by processor 42.

Note that transfer of information from the external device 40 to the internal memory 34, and vice versa, may be by electrical conductor or by wireless radio frequency (RF) transmission (over the air and through the body). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example.

The external device 40 could be a patient's external device that has an external wireline interface 54 which provides an interface between the external device 40 and a clinician's device 56. The clinician's device might, for example, have a USB port and wireline interface 54 might include a USB port, so that a USB cable may connect the two ports. The clinician's device 56 may read data from the external device 40 and write information and control signaling to the external device 40, in some embodiments. In the alternative to a wireline connection, the wireline interface 54 could include or be replaced by a radio interface.

In some embodiments, the external power transmitter 25 may be in electrical communication with the processing circuitry 46.

Note that although the internal components are shown to include an LVAD pump 12, in some embodiments, one or more other internal devices that require electrical power are implemented instead of or in addition to the LVAD pump 12.

Figure 3:
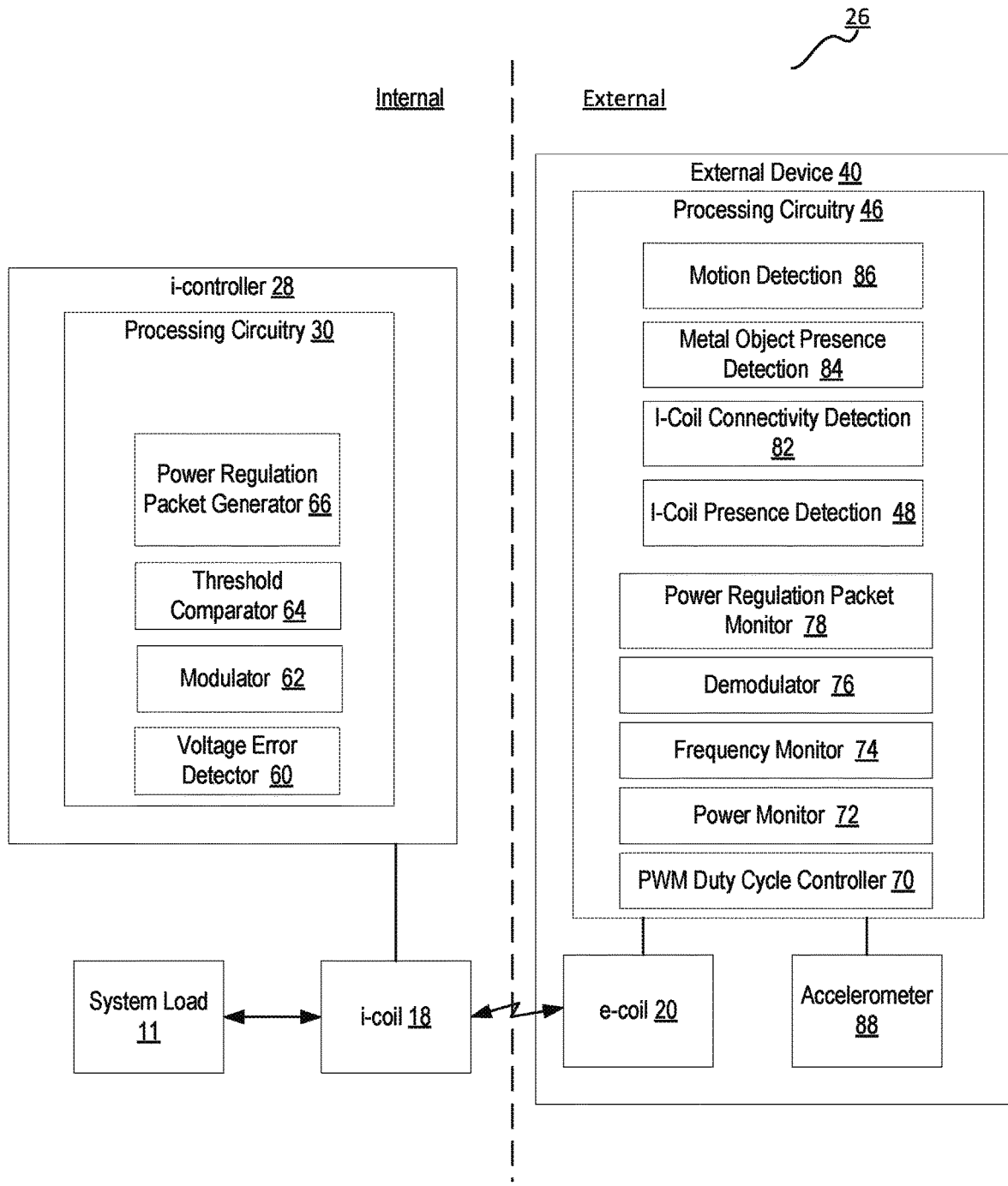
FIG. 3 is a more detailed block diagram of the processing circuitry of the LVAD implant system of FIG. 2.

FIG. 3 shows a more detailed view of the processing circuitry 30 of the i-controller 28 and the processing circuitry 46 of the external device 40. In FIG. 3, some of the internal and external components of the implant system 26 are omitted for clarity. Also, a system load block 11 is shown connected to the i-coil 18. The system load 11 may be or include the LVAD pump 12 or other implanted load device and may also include the load presented by other internal components, including the i-controller 28.

In the processing circuitry 30 of the i-controller 28, a voltage error detector 60 is configured to determine a difference between the voltage received at the i-coil 18 and a predetermined target voltage set by the processing circuitry 30. This difference is a voltage error that may be modulated by the modulator 62 to be carried via a time-varying signal applied to the i-coil 18. The i-coil transmits the voltage error-carrying signal to the external device 40 to inform the external device 40 of the voltage error so that the voltage applied to the e-coil 20 may be adjusted in a direction calculated to drive the voltage error toward zero.

The processing circuitry 30 may also include a threshold comparator 64 configured to compare the received voltage at the i-coil 18 to a voltage threshold to determine whether to send power regulation packets generated by the power regulation packet generator 66 to the external device. When the received voltage at the i-coil 18 exceeds the voltage threshold, power regulation packets are sent to the external device 40.

In the processing circuitry 46 of the external device 40, a pulse width modulation duty cycle controller 70 is configured to modulate or adjust the power delivered to the e-coil 20 by the external power transmitter 25. A power monitor 72 monitors the power drawn by the e-coil 20 to determine if the e-coil 20 is drawing additional power for a given drive current, as this may be indicative of the presence of a metal object. A frequency monitor 74 monitors the resonance frequency of the e-coil 20 to determine the presence and connectivity of the i-coil 18. Note that when reference is made herein to the resonance frequency of the e-coil 20, it will be understood that this resonance frequency may be of a circuit including the e-coil 20 that may also include other circuit components such as capacitors.

A demodulator 76 demodulates the signal received by the e-coil 20. The demodulated signal may include a voltage error value and/or power regulation packets generated by the power regulation packet generator 66. A power regulation packet monitor 78 monitors the demodulated signal to detect the presence of power regulation packets.

The processing circuitry 46 may perform one or more algorithms described in more detail below with reference to FIGS. 4-7. The i-coil presence detection algorithm (PDA) 48 attempts to detect the presence of the i-coil 18. The i-coil connectivity algorithm attempts to determine i-coil connectivity to protect diodes that prevent current overload to protect implanted components and the patient. The metal object detection algorithm 84 attempts to detect the presence of a metal object. The motion detection algorithm 86 attempts to detect whether the e-coil is in motion and to adjust a frequency of i-coil detection attempts depending on whether the e-coil is in motion.

Note that some or all of the blocks shown within the processing circuitry 46 may be performed within the external power transmitter 25 or in a different location within the external device 40.

Figure 4:
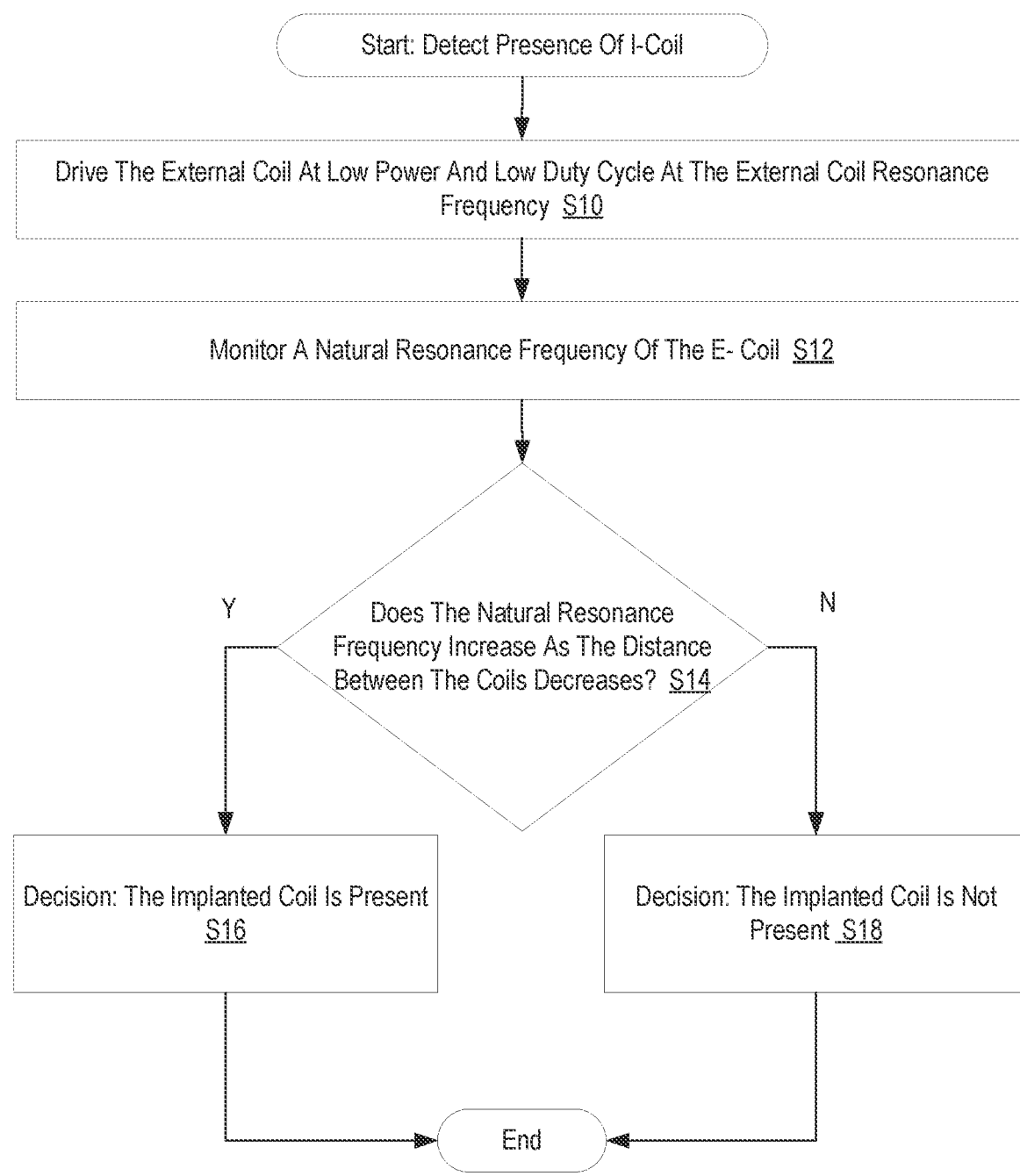
FIG. 4 is a flowchart of an exemplary process for detecting presence of an internal coil.

FIG. 4 is a flowchart of an exemplary process for detecting, by the external device 40, the presence of the i-coil 18. In Block S10 of the process, the e-coil 20 is driven by the external power transmitter 25 at a low power and low duty cycle at a resonance frequency of the e-coil 20. In Block S12, the resonance frequency of the e-coil 20 is monitored by the frequency monitor 74. If, at Block S14, it is observed by the monitoring that the resonance frequency of the e-coil 20 increases as the e-coil 20 is moved closer to the body toward the expected location of the i-coil 18, then at Block S16, the decision is made that the i-coil 18 is present. Otherwise, a decision is made at Block S18 that the i-coil 18 is not present. Note that when the i-coil 18 is not present, the resonance frequency of the e-coil does not change when the e-coil 20 is moved closer to the general area where the i-coil 18 is expected to be.

Figure 5:
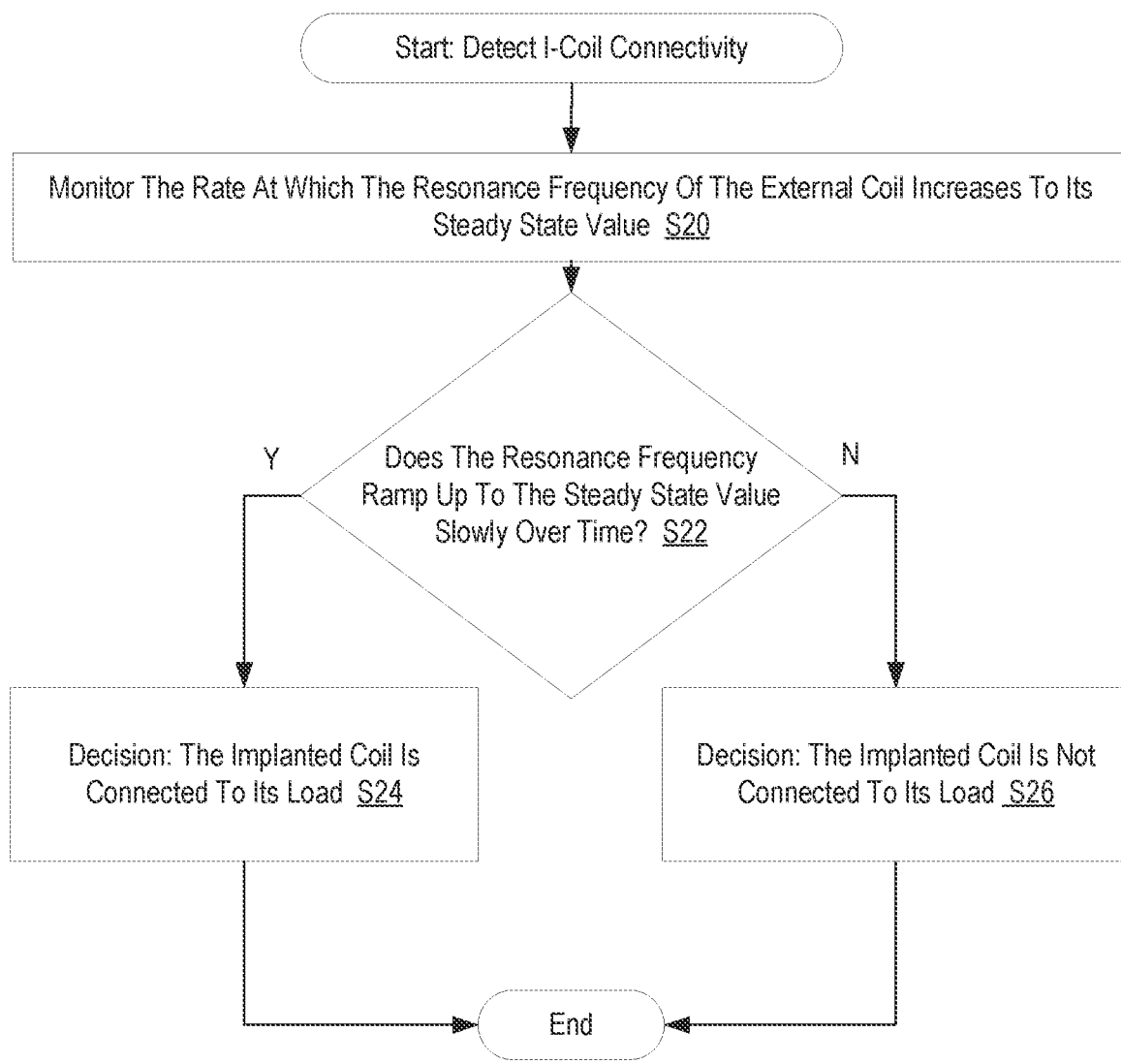
FIG. 5 is a flowchart of an exemplary process for detecting connectivity of an internal coil.

FIG. 5 is a flowchart of an exemplary process for detecting, by the external device 40, whether the i-coil 18 is connected to the system load 11. This process may logically follow completion of the process of detecting the presence of the i-coil 18 shown in FIG. 4, in some embodiments. In Block S20, the rate at which the resonance frequency of the e-coil 20 increases to its steady state value is monitored by the frequency monitor 74. If the resonance frequency ramps up to its steady state value slowly over time, as determined at Block S22, the decision is made that the i-coil 18 is connected to the system load 11 (Block S24). In some embodiments, the rate of increase of the resonance frequency toward the steady state value is compared to a rate threshold and if the rate of increase is less than the rate threshold, the decision is made that the i-coil 18 is connected to the system load 11. If instead, for example, the resonance frequency jumps quickly to its steady state value, then the decision is made that the i-coil 18 is not connected to the system load 11 (Block S26).

Figure 6:
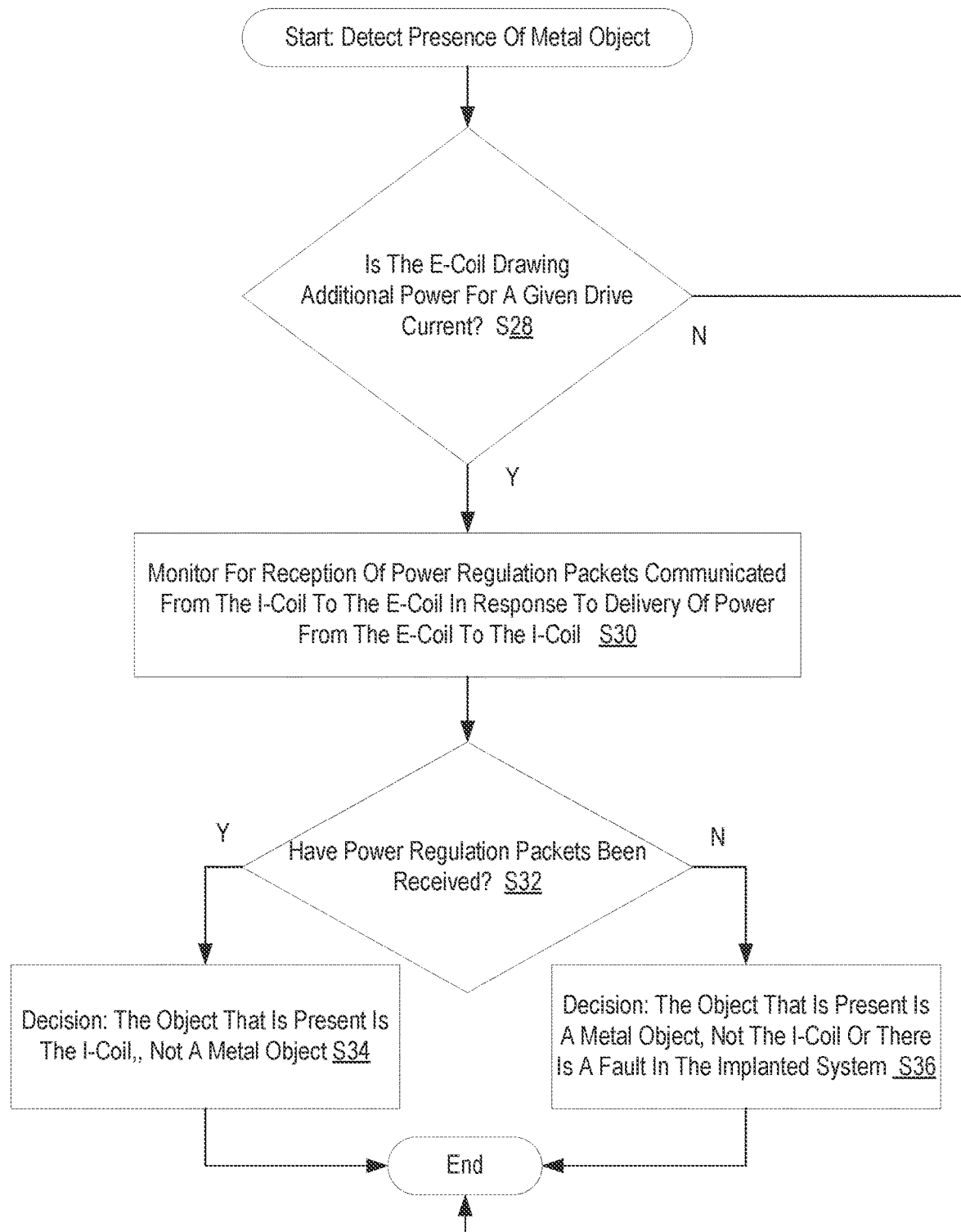
FIG. 6 is a flowchart of an exemplary process for detecting presence of a metal object.

FIG. 6 is flowchart of an exemplary process for detecting presence of a metal object. In Block S28, the power monitor 72 determines whether the e-coil 20 is drawing additional power for a given drive current (which is an indication of the possible presence of a metal object.) For example, the processing circuitry 46 may compare the power drawn by the e-coil 20 to a power threshold corresponding to the drive current applied to the e-coil 20. If the e-coil 20 is drawing additional power for a given drive current, then, in Block S30, the power regulation packet monitor 78 monitors for reception of power regulation packets received from the power regulation packet generator 66, via the i-coil 18. These power regulation packets are generated via the power regulation packet generator 66 once the received voltage at the i-coil 18 exceeds a threshold, to confirm to the external device 40 that power is being received. If the power regulation packets are being received, at Block S32, then a decision is made at Block S34 that the object that is present is the i-coil 18, not a metal object. Otherwise, at Block S136, a decision is made that the object that is present is a metal object rather than the i-coil 18, or there is a fault in the implanted system.

Figure 7:
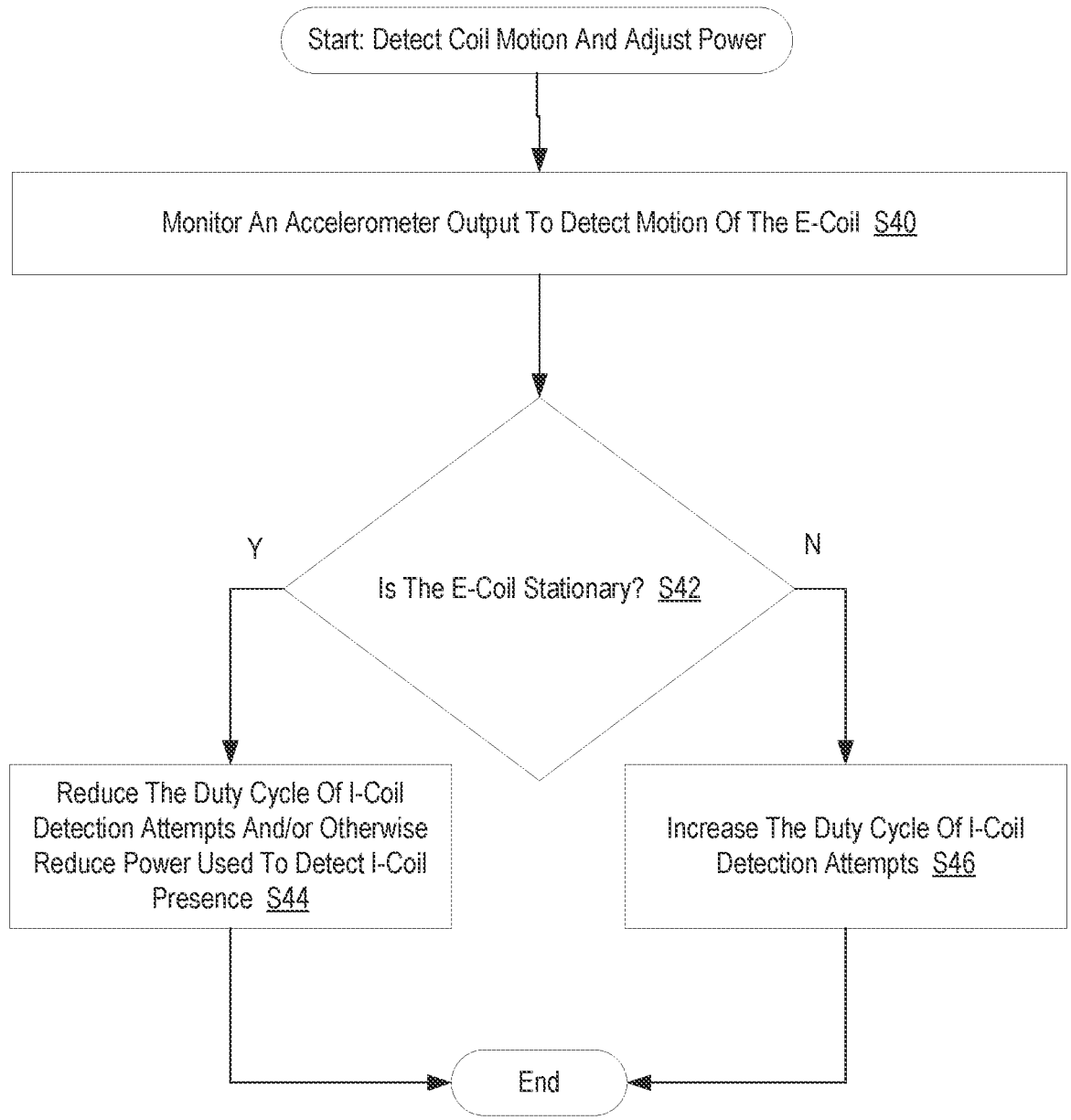
FIG. 7 is a flowchart of an exemplary process for determining motion of an external device and adjusting a duty cycle of internal coil detection attempts.

FIG. 7 is a flowchart of an exemplary process for detecting coil motion and adjusting power delivered to the i-coil 18. In Block S49, an output of the accelerometer 88 is monitored to detect acceleration (indicative of motion) of the e-coil 20. If the e-coil 20 is stationary (no acceleration), as determined at Block S42, then it may be assumed that that the e-coil 20 is not being held or worn. In this case, the duty cycle or frequency of attempts to detect the presence of the i-coil 18 may be reduced by the pulse width modulation (PWM) duty cycle controller 70 (Block S44), or power used to detect the presence of the i-coil 18 may otherwise be reduced. If the e-coil 20 is not stationary (acceleration is detected), then the duty cycle of the i-coil detection attempts may be increased (Block S46).

Note that some or all of the steps of the processes shown in FIGS. 4-7 may be implemented by execution of software instructions by the processor 42 of the external device 40.

Figure 8:
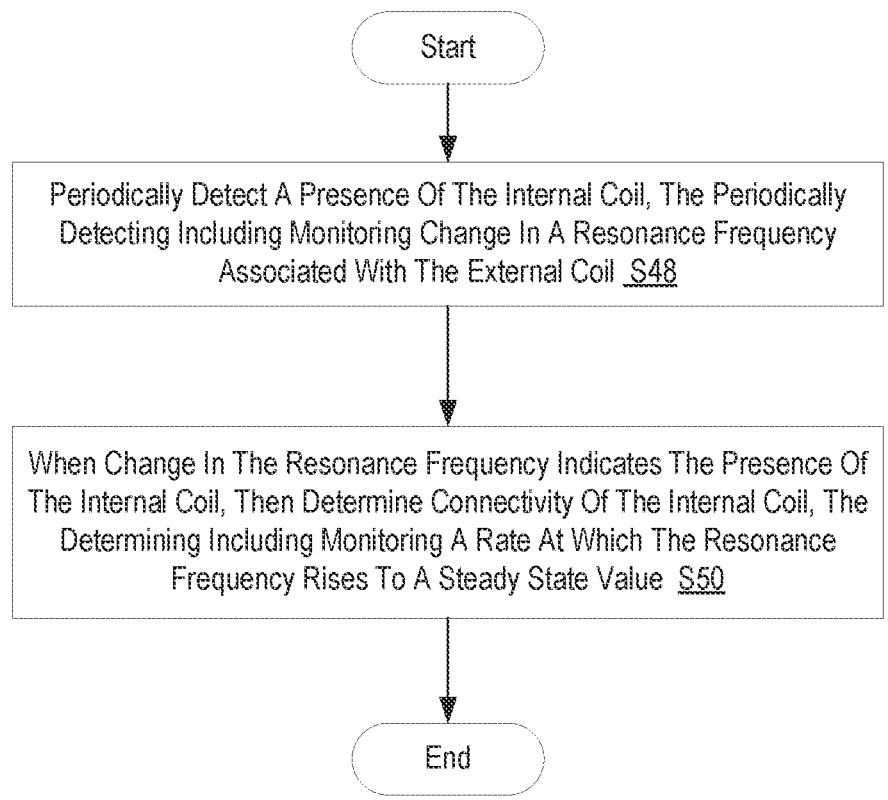
FIG. 8 is a flowchart of an exemplary process for detecting presence and connectivity of an internal coil.

FIG. 8 is a flowchart of an exemplary process for determining the presence and connectivity of an internal coil in a medical implant system. The process includes periodically detecting a presence of the internal coil, the periodically detecting including monitoring change in a resonance frequency associated with the external coil (Block S48). The process also includes, when change in the resonance frequency indicates the presence of the internal coil, then determining connectivity of the internal coil, the determining including monitoring a rate at which the resonance frequency rises to a steady state value (Block S50).

Thus, to conserve power, the e-coil 20 may be driven at low power and with a low duty cycle. The e-coil 20 may be driven at a resonance frequency, while monitoring the resonance frequency. If the i-coil 18 is not present, the driving frequency will be the tuned frequency of the e-coil 20. If the i-coil 18 is present, the resonant frequency of the e-coil 20 increases as the distance between the coils decreases. By monitoring the resonance frequency of the e-coil 20, presence or absence of the i-coil 18 can be detected.

Rate of change of the resonance frequency of the e-coil 20 may also be monitored to determine if the i-coil 18 is connected to the load 11. If the i-coil 18 is not connected to the load 11, the frequency will jump to the steady state value quickly. If the i-coil 18 is connected to the load 11, the frequency will ramp up to a steady state value as the energy storage capacitors internal to the i-controller 28 battery 16 are charged up to the regulation voltage. If an unconnected i-coil 18 is detected, application of power to the e-coil 20 may be quickly stopped or lowered so that protection diodes are not overheated. By monitoring the rate at which the resonance frequency rises to its steady state value, whether the i-coil 18 is connected to the system load 11 can be detected.

The input power to the coil may be monitored to determine if there is a metal object present. When a metal object is present there will be eddy currents induced in the metal which will draw additional power to drive the e-coil 20 at a given drive current. Depending on the magnitude of the additional power, the duty cycle of the drive voltage used to detect the i-coil 18 may be reduced or the duration of a burst of the drive voltage may be reduced to reduce or minimize heating of the metal object and to reduce a drain on the external battery 24. While driving the e-coil 20, the power regulation packet monitor 78 monitors the signal received from demodulator 76. The demodulator 76 demodulates the signal modulated onto the i-coil signal by the modulator 62. If the signal modulated onto the i-coil signal contains power regulation packets, these power regulation packets will be sent to the e-coil 20, once the received voltage at the i-coil 18 exceeds the voltage threshold. The power regulation packets serve to confirm to the external device 40 that power is being received via the i-coil 18. Absence of these power regulation packets indicates that the power delivered by the e-coil 20 is being delivered to a metal object rather than to the i-coil 18, and/or there is a fault in the implanted system.

To further save power, the accelerometer 88 may be used to detect when the e-coil 20 is being moved. When the e-coil 20 is being moved, the duty cycle of the i-coil detection attempts may be increased. If the e-coil 20 is not being worn, the output of the accelerometer 88 may be expected to be low. In such case, the frequency or duty cycle of the attempts to detect the i-coil 18 may be decreased.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method implemented by a medical implant system having an internal coil implanted within a body of a patient, the internal coil capable of receiving power from an external coil outside the body, the external coil in communication with external processing circuitry configured to perform steps of the method, the method comprising:
   detecting a presence of the internal coil based upon a coil detection duty cycle;
   determining acceleration of an external component of the medical implant system based upon an output from an accelerometer; and
   responsive to acceleration being detected, adjusting the coil detection duty cycle based upon the output from the accelerometer.

2. The method of claim 1, wherein detecting the presence of the internal coil comprises monitoring a change in a resonance frequency associated with the external coil and the internal coil.

3. The method of claim 2, wherein when a distance between an expected location of the internal coil and a location of the external coil decreases, the resonance frequency increases.

4. The method of claim 2, wherein when a distance between an expected location of the internal coil and a location of the external coil increases, the resonance frequency decreases.

5. The method of claim 4, further comprising:
   responsive to the resonance frequency indicating the presence of the internal coil, monitoring a rate at which the resonance frequency rises to a steady state value; and
   determining a connectivity of the internal coil based upon the rate at which the resonance frequency rises to the steady state value.

6. The method of claim 5, further comprising: responsive to the resonance frequency increasing to the steady state value at a rate that falls below a rate threshold, determining that the internal coil is connected to an internal load.

7. The method of claim 1, further comprising detecting a presence of a metal object based upon whether the external coil is drawing increased power for a given drive current and based upon reception of power regulation packets from the internal coil.

8. The method of claim 7, wherein detecting the presence of the metal object comprises: responsive to no reception of the power regulation packets within a time interval, determining that the metal object is present.

9. The method of claim 7, further comprising: responsive to no reception of the power regulation packets within a time interval, determining that there is a fault in one or more internal components of the medical implant system.

10. The method of claim 1, wherein adjusting the coil detection duty cycle based upon the output from the accelerometer comprises:
    increasing the coil detection duty cycle in response to the output from the accelerometer being high; and
    decreasing the coil detection duty cycle in response to the output from the accelerometer being low.

11. A medical implant system comprising:
    an external coil outside a body of a patient, wherein an internal coil implanted within the body of the patient is configured to receive power from the external coil;
    an accelerometer configured to detect acceleration of the external coil;
    processing circuitry configured to:
        communicate with the external coil;
        detect a presence of the internal coil based upon a coil detection duty cycle;
        determine acceleration of the external coil based upon an output from the accelerometer; and
        responsive to acceleration being detected, adjust the coil detection duty cycle based upon the output from the accelerometer.

12. The medical implant system of claim 11, wherein the external processing circuitry is configured to adjust the coil detection duty cycle based upon the output from the accelerometer by:
    increasing the coil detection duty cycle in response to the output from the accelerometer being greater than zero; and
    decreasing the coil detection duty cycle in response to the output from the accelerometer being zero.

13. The medical implant system of claim 11, wherein the processing circuitry is configured to detect the presence of the internal coil by monitoring a change in a resonance frequency associated with the external coil and the internal coil.

14. The medical implant system of claim 13, wherein when a distance between an expected location of the internal coil and a location of the external coil decreases, the resonance frequency increases.

15. The medical implant system of claim 13, wherein when a distance between an expected location of the internal coil and a location of the external coil increases, the resonance frequency decreases.

16. The medical implant system of claim 15, wherein the external processing circuitry is further configured to:
    responsive to the resonance frequency indicating the presence of the internal coil, monitor a rate at which the resonance frequency rises to a steady state value;
    determine a connectivity of the internal coil based upon the rate at which the resonance frequency rises to the steady state value.

17. The medical implant system of claim 16, wherein the external processing circuitry is further configured to: responsive to the resonance frequency increasing to the steady state value at a rate that falls below a rate threshold, determine that the internal coil is connected to an internal load.

18. The medical implant system of claim 11, wherein the external processing circuitry is further configured to: detect a presence of a metal object based upon whether the external coil is drawing increased power for a given drive current and reception of power regulation packets from the internal coil.

19. The medical implant system of claim 18, wherein the external processing circuitry is configured to detect the presence of the metal object by: responsive to no reception of the power regulation packets within a time interval, determine that the metal object is present.

20. The medical implant system of claim 18, wherein the external processing circuitry is further configured to: responsive to no reception of the power regulation packets within a time interval, determine that there is a fault in one or more internal components of the medical implant system.

21. The medical implant system of claim 11, further comprising the internal coil.

22. The medical implant system of claim 11, wherein the external processing circuitry is configured to adjust the coil detection duty cycle based upon the output from the accelerometer by:
   increasing the coil detection duty cycle in response to the output from the accelerometer being greater than a threshold; and
   decreasing the coil detection duty cycle in response to the output from the accelerometer being less than the threshold.

* * * * *